(12) United States Patent
McKay

(10) Patent No.: US 9,364,583 B2
(45) Date of Patent: Jun. 14, 2016

(54) OSTEOINDUCTIVE DEMINERALIZED BONE IMPLANT

(71) Applicant: Warsaw Orthopedic, Inc., Warsaw, IN (US)

(72) Inventor: William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 14 days.

(21) Appl. No.: 14/261,986

(22) Filed: Apr. 25, 2014

(65) Prior Publication Data

US 2015/0306278 A1    Oct. 29, 2015

(51) Int. Cl.
| | |
|---|---|
| *A61K 35/32* | (2015.01) |
| *A61L 27/36* | (2006.01) |
| *A61L 27/24* | (2006.01) |
| *A61L 27/48* | (2006.01) |
| *A61L 27/56* | (2006.01) |

(52) U.S. Cl.
CPC .............. *A61L 27/3608* (2013.01); *A61L 27/24* (2013.01); *A61L 27/3683* (2013.01); *A61L 27/48* (2013.01); *A61L 27/56* (2013.01); *A61L 2430/02* (2013.01)

(58) Field of Classification Search
CPC ............ A61L 27/3608; A61L 27/3683; A61L 2430/01; A61L 27/24; A61L 27/48; A61L 27/562; A61K 35/32
See application file for complete search history.

(56) References Cited

U.S. PATENT DOCUMENTS

| | | | |
|---|---|---|---|
| 4,646,795 A | 3/1987 | Hebron et al. | |
| 5,202,021 A | 4/1993 | Griffin et al. | |
| 5,353,531 A | 10/1994 | Doucette | |
| 5,716,087 A | 2/1998 | Backich et al. | |
| 5,738,399 A | 4/1998 | Mitchell | |
| 6,294,187 B1 | 9/2001 | Boyce et al. | |
| 6,440,444 B2 | 8/2002 | Boyce et al. | |
| 6,478,825 B1 | 11/2002 | Winterbottom et al. | |
| 6,696,073 B2 | 2/2004 | Boyce et al. | |
| 6,723,131 B2 | 4/2004 | Muschler | |
| 7,083,648 B2 | 8/2006 | Yu et al. | |
| 7,097,027 B1 | 8/2006 | Chen | |
| 7,191,553 B2 | 3/2007 | Doucette et al. | |
| 7,387,507 B2 | 6/2008 | Schuler | |
| 8,042,688 B2 | 10/2011 | Parks et al. | |
| 8,100,452 B1 | 1/2012 | Homewood | |
| 2005/0251267 A1 | 11/2005 | Winterbottom et al. | |
| 2005/0283255 A1 | 12/2005 | Geremakis et al. | |
| 2006/0052879 A1 | 3/2006 | Kolb | |
| 2006/0216323 A1 | 9/2006 | Knaack et al. | |
| 2007/0088443 A1 | 4/2007 | Hanssen et al. | |
| 2007/0098756 A1 | 5/2007 | Behnam | |
| 2007/0110820 A1 | 5/2007 | Behnam | |
| 2007/0191963 A1 | 8/2007 | Winterbottom et al. | |
| 2009/0130173 A1 | 5/2009 | Behnam et al. | |
| 2009/0192474 A1 | 7/2009 | Wei et al. | |
| 2009/0234277 A1 | 9/2009 | Wei et al. | |

(Continued)

*Primary Examiner* — Abigail Fisher
(74) *Attorney, Agent, or Firm* — Sorell Lenna & Schmidt LLP

(57) ABSTRACT

A bone graft delivery device is provided comprising: a porous biodegradable graft body for inducing bone growth at a surgical site, the porous biodegradable graft body having demineralized bone matrix (DBM) fibers disposed within the porous biodegradable body, and DBM powder disposed adjacent to, on or in the DBM fibers, wherein the porous biodegradable graft body facilitates transfer of cells into and out of the porous biodegradable graft body to induce bone growth at the surgical site. Methods of making the device and using the device are also disclosed.

20 Claims, 1 Drawing Sheet

(56) References Cited

U.S. PATENT DOCUMENTS

| | | |
|---|---|---|
| 2009/0240255 A1 | 9/2009 | McKay et al. |
| 2010/0203155 A1 | 8/2010 | Wei et al. |
| 2011/0054408 A1 | 3/2011 | Wei et al. |
| 2011/0071536 A1 | 3/2011 | Kleiner et al. |
| 2011/0152754 A1 | 6/2011 | Cantor et al. |
| 2012/0097556 A1 | 4/2012 | Gascoine |
| 2012/0121660 A1* | 5/2012 | Akella et al. ................ 424/400 |
| 2012/0297902 A1 | 11/2012 | Leventhal et al. |
| 2014/0277569 A1* | 9/2014 | Lange .................. A61F 2/28 623/23.51 |

* cited by examiner

OSTEOINDUCTIVE DEMINERALIZED BONE IMPLANT

BACKGROUND

The use of bone grafts and bone substitute materials in orthopedic medicine is known. While bone wounds can regenerate without the formation of scar tissue, fractures and other orthopedic injuries take a long time to heal, during which time the bone is unable to support physiologic loading unaided. Metal pins, screws, rods, plates and meshes are frequently required to replace the mechanical functions of injured bone. However, metal is significantly more stiff than bone. Use of metal implants may result in decreased bone density around the implant site due to stress shielding. Physiologic stresses and corrosion may cause metal implants to fracture. Unlike bone, which can heal small damage cracks through remodeling to prevent more extensive damage and failure, damaged metal implants can only be replaced or removed. The natural cellular healing and remodeling mechanisms of the body coordinate removal of bone and bone grafts by osteoclast cells and formation of bone by osteoblast cells.

Conventionally, bone tissue regeneration is achieved by filling a bone repair site with a bone graft. Over time, the bone graft is incorporated by the host and new bone remodels the bone graft. In order to place the bone graft, it is common to use a monolithic bone graft or to form an osteoimplant comprising particulated bone in a carrier. The carrier is thus chosen to be biocompatible, to be resorbable, and to have release characteristics such that the bone graft is accessible.

The rapid and effective repair of bone defects caused by injury, disease, wounds, or surgery is a goal of orthopedic surgery. Toward this end, a number of compositions and materials have been used or proposed for use in the repair of bone defects. The biological, physical, and mechanical properties of the compositions and materials are among the major factors influencing their suitability and performance in various orthopedic applications.

Autologous cancellous bone ("ACB"), also known as autograft or autogenous bone, is considered the gold standard for bone grafts. ACB is osteoinductive and nonimmunogenic, and, by definition, has all of the appropriate structural and functional characteristics appropriate for the particular recipient. Unfortunately, ACB is only available in a limited number of circumstances. Some individuals lack ACB of appropriate dimensions and quality for transplantation, and donor site pain and morbidity can pose serious problems for patients and their physicians.

Much effort has been invested in the identification or development of alternative bone graft materials. Demineralized bone matrix ("DBM") implants have been reported to be particularly useful. Demineralized bone matrix is typically derived from cadavers. The bone is removed aseptically and/or treated to kill any infectious agents. The bone is then particulated by milling or grinding and then the mineral components are extracted for example, by soaking the bone in an acidic solution.

DBM is a desirable component of bone graft materials because it provides an osteoinductive matrix and exhibits osteoconductive potential, thereby promoting bone growth and healing. DBM is osteoinductive due to the presence of active bone growth factors including bone morphogenic proteins (BMP). Osteoinductivity depends not only on the concentration of growth factors in DBM, but also on their availability to cells after implantation. Moreover, DBM is fully resorbable, and bone graft materials containing organic DBM are highly biocompatible because it contains many of the components of natural bone. Following implantation, the presence of DBM induces cellular recruitment to the site of injury. The recruited cells may eventually differentiate into bone forming cells. Such recruitment of cells leads to an increase in the rate of wound healing and, therefore, to faster recovery for the patient. Advantageously, DBM costs less than many other available organic bone composition additives, such as isolated BMPs.

Some DBM formulations have various drawbacks. For example, while the collagen-based matrix of DBM is relatively stable, the active factors within the DBM matrix are rapidly degraded. The osteogenic activity of the DBM may be significantly degraded within 24 hours after implantation, and in some instances the osteogenic activity may be inactivated within 6 hours. Therefore, the factors associated with the DBM are only available to recruit cells to the site of injury for a short time after transplantation. For much of the healing process, which may take weeks to months, the implanted material may provide little or no assistance in recruiting cells.

Attempts to overcome these problems have lead researchers to utilize delivery devices such as polymer mesh bags to release DBM at a surgical site. However, any additional bone graft material, such as for example, autologous bone or growth factors, would have to be placed underneath or on top of the DBM mesh bag which is, typically, not recommended for inducing new bone formation.

Moreover, when DBM particles are dispersed throughout the mesh bag, gaps can exist between the DBM particles. These gaps can be larger than the "jumping distance" of osteoblasts, and cells in these gaps will not receive an adequate osteoinductive signal.

Thus, there is a need to improve the efficacy and consistency of DBM delivery devices by mixing the DBM particles/fibers with other bone graft materials such as DBM powders, autologous bone and other therapeutic agents throughout the mesh bag prior to, during or after the surgical procedure. It would therefore be desirable to provide delivery devices that increase the content of DBM, increase the surface area of the DBM, and uniformly distribute the DBM throughout the delivery device to enhance bone growth when the delivery device is implanted at a bone defect.

SUMMARY

The bone implant devices and methods according to the present application increase DBM content in the device, increase the surface area of the DBM, and uniformly distribute the DBM throughout the delivery device to enhance bone growth when the delivery device is implanted at a bone defect. The bone implant devices and methods provided enhance bone growth by reducing the gaps that may exist between the DBM particles and reduce the distance for cells (e.g., osteoclasts, osteoblasts, etc.) to travel throughout the device to allow those cells to receive an adequate osteoinductive signal as opposed to only along the surface of the device. In some embodiment, the device improves the fusion of adjacent interspinous processes, vertebral bodies, bone defects and/or fractures.

According to one aspect, there is a bone graft delivery device comprising: a porous biodegradable graft body for inducing bone growth at a surgical site, the porous biodegradable graft body having demineralized bone matrix (DBM) fibers disposed within the porous biodegradable body, and DBM powder disposed adjacent to, on or in the DBM fibers, wherein the porous biodegradable graft body facilitates transfer of cells into and out of the porous biodegradable graft body to induce bone growth at the surgical site.

According to another aspect, there is a bone graft delivery device comprising: a porous biodegradable graft body for inducing bone growth at a surgical site, the porous biodegradable graft body having demineralized bone matrix (DBM) fibers and DBM powder suspended in a polymer matrix that is disposed within the porous biodegradable body, wherein the porous biodegradable graft body facilitates transfer of cells into and out of the porous biodegradable graft body to induce bone growth at the surgical site.

According to yet another aspect, there is a method of making a bone graft delivery device, the method comprising: adding DBM fibers to DBM powder to form a mixture; adding the mixture of DBM fibers and the DBM powder to a collagen slurry; drying the collagen slurry to form a sponge; and disposing the sponge within a biodegradable mesh bag. In some embodiments, the sponge is not disposed within the biodegradable mesh sealed bag.

While multiple embodiments are disclosed, still other embodiments of the present application will become apparent to those skilled in the art from the following detailed description, which is to be read in connection with the accompanying drawings. As will be apparent, the present disclosure is capable of modifications in various obvious aspects, all without departing from the spirit and scope of the present disclosure. Accordingly, the detailed description is to be regarded as illustrative in nature and not restrictive.

Figure 1:
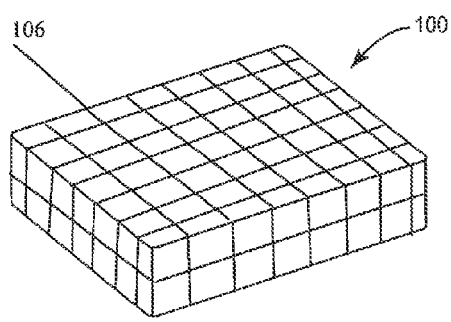
FIG. 1 depicts a perspective view of an exemplary bone graft delivery device according to an aspect of the present application.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

Definitions

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Similarly, when values are expressed as approximations, by use of the antecedent "about," it will be understood that the particular value forms another embodiment that is +/−10% of the recited value. Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value.

Notwithstanding that the numerical ranges and parameters setting forth the broad scope of this application are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Bioactive agent or bioactive compound is used herein to refer to a compound or entity that alters, inhibits, activates, or otherwise affects biological or chemical events. For example, bioactive agents may include, but are not limited to, osteogenic or chondrogenic proteins or peptides, anti-AIDS substances, anti-cancer substances, antibiotics, immunosuppressants, anti-viral substances, enzyme inhibitors, hormones, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, angiogenic factors, anti-secretory factors, anticoagulants and/or antithrombotic agents, local anesthetics, ophthalmics, prostaglandins, anti-depressants, anti-psychotic substances, anti-emetics, and imaging agents. In certain embodiments, the bioactive agent is a drug. Bioactive agents further include RNAs, such as siRNA, and osteoclast stimulating factors. In some embodiments, the bioactive agent may be a factor that stops, removes, or reduces the activity of bone growth inhibitors. In some embodiments, the bioactive agent is a growth factor, cytokine, extracellular matrix molecule or a fragment or derivative thereof, for example, a cell attachment sequence such as RGD. A more complete listing of bioactive agents and specific drugs suitable for use in the present application may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", edited by Susan Budavari et al., CRC Press, 1996; and the United States Pharmacopeia-25/National Formulary-20, published by the United States Pharmacopeia Convention, Inc., Rockville Md., 2001, each of which is incorporated herein by reference.

Biocompatible, as used herein, is intended to describe materials that, upon administration in vivo, do not induce undesirable long-term effects.

Bone, as used herein, refers to bone that is cortical, cancellous or cortico-cancellous of autogenous, allogenic, xenogenic, or transgenic origin.

Bone graft, as used herein, refers to any implant prepared in accordance with the embodiments described herein and therefore may include expressions such as bone material and bone membrane.

Demineralized, as used herein, refers to any material generated by removing mineral material from tissue, for example, bone tissue. In certain embodiments, the demineralized compositions described herein include preparations containing less than 5% calcium. In some embodiments, the demineralized compositions may comprise less than 1% calcium by weight. In some embodiments, the compositions may comprise less than 5, 4, 3, 2 and/or 1% calcium by weight. Partially demineralized bone is intended to refer to preparations with greater than 5% calcium by weight but containing less than 100% of the original starting amount of calcium. In some embodiments, partially demineralized bone comprises 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and/or 99% of the original starting amount of calcium.

In some embodiments, demineralized bone has less than 95% of its original mineral content. In some embodiments, demineralized bone has less than 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6 and/or 5% of its original content. In some embodiments, "Demineralized" is intended to encompass such expressions as "substantially demineralized," "partially demineralized," "surface demineralized," and "fully demineralized." "Partially demineralized" is intended to encompass "surface demineralized."

In some embodiments, the demineralized bone may be surface demineralized from about 1-99%. In some embodiments, the demineralized bone is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and/or 99% surface demineralized. In various embodiments, the demineralized bone may be surface demineralized from about 15-25%. In some embodiments, the demineralized bone is 15, 16, 17, 18, 19, 20, 21, 22, 23, 24 and/or 25% surface demineralized.

Demineralized bone activity refers to the osteoinductive activity of demineralized bone.

Demineralized bone matrix (DBM), as used herein, refers to any material generated by removing mineral material from bone tissue. In some embodiments, the DBM compositions as used herein include preparations containing less than 5% calcium and, in some embodiments, less than 1% calcium by weight. In some embodiments, the DBM compositions include preparations that contain less than 5, 4, 3, 2 and/or 1% calcium by weight. In other embodiments, the DBM compositions comprise partially demineralized bone (e.g., preparations with greater than 5% calcium by weight but containing less than 100% of the original starting amount of calcium).

Osteoconductive, as used herein, refers to the ability of a substance to serve as a template or substance along which bone may grow.

Osteogenic, as used herein, refers to materials containing living cells capable of differentiation into bone tissue.

Osteoinductive, as used herein, refers to the quality of being able to recruit cells from the host that have the potential to stimulate new bone formation. Any material that can induce the formation of ectopic bone in the soft tissue of an animal is considered osteoinductive. For example, most osteoinductive materials induce bone formation in athymic rats when assayed according to the method of Edwards et al., "Osteoinduction of Human Demineralized Bone: Characterization in a Rat Model," Clinical Orthopaedics & Rel. Res., 357:219-228, December 1998, incorporated herein by reference.

Superficially demineralized, as used herein, refers to bone-derived elements possessing at least about 90 weight percent of their original inorganic mineral content. In some embodiments, superficially demineralized contains at least about 90, 91, 92, 93, 94, 95, 96, 97, 98 and/or 99 weight percent of their original inorganic material. The expression "partially demineralized" as used herein refers to bone-derived elements possessing from about 8 to about 90 weight percent of their original inorganic mineral content. In some embodiments, partially demineralized contains about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89 and/or 90 weight percent of their original inorganic mineral content. The expression "fully demineralized" as used herein refers to bone containing less than 8% of its original mineral context. In some embodiments, fully mineralized contains about less than 8, 7, 6, 5, 4, 3, 2 and/or 1% of its original mineral content.

The expression "average length to average thickness ratio" as applied to the DBM fibers of the present application means the ratio of the longest average dimension of the fiber (average length) to its shortest average dimension (average thickness). This is also referred to as the "aspect ratio" of the fiber.

Fibrous, as used herein, refers to bone elements whose average length to average thickness ratio or aspect ratio of the fiber is from about 50:1 to about 1000:1. In some embodiments, average length to average thickness ratio or aspect ratio of the fiber is from about 50:1, 75:1, 100:1, 125:1, 150:1, 175:1, 200:1, 225:1, 250:1, 275:1, 300:1, 325:1, 350:1, 375:1, 400:1, 425:1, 450:1, 475:1, 500:1, 525:1, 550:1, 575:1, 600:1, 625:1, 650:1, 675:1, 700:1, 725:1, 750:1, 775:1, 800:1, 825:1, 850:1, 875:1, 900:1, 925:1, 950:1, 975:1 and/or 1000:1. In overall appearance the fibrous bone elements can be described as bone fibers, threads, narrow strips, or thin sheets. Often, where thin sheets are produced, their edges tend to curl up toward each other. The fibrous bone elements can be substantially linear in appearance or they can be coiled to resemble springs. In some embodiments, the bone fibers are of irregular shapes including, for example, linear, serpentine or curved shapes. The bone fibers are preferably demineralized however some of the original mineral content may be retained when desirable for a particular embodiment. In various embodiments, the bone fibers are mineralized. In some embodiments, the fibers are a combination of demineralized and mineralized.

Non-fibrous, as used herein, refers to elements that have an average width substantially larger than the average thickness of the fibrous bone element or aspect ratio of less than from about 50:1 to about 1000:1. Preferably the non-fibrous bone elements are shaped in a substantially regular manner or specific configuration, for example, triangular prism, sphere, cube, cylinder and other regular shapes. By contrast, particles such as chips, shards, or powders possess irregular or random geometries. It should be understood that some variation in dimension will occur in the production of the elements of this application and elements demonstrating such variability in dimension are within the scope of this application and are intended to be understood herein as being within the boundaries established by the expressions "mostly irregular" and "mostly regular".

The bone implant devices and methods according to the present application increase DBM content in the device, increase the surface area of the DMB, and uniformly distribute the DBM throughout the delivery device to enhance bone growth when the delivery device is implanted at a bone defect. The bone implant devices and methods provided enhance bone growth by reducing the gaps that may exist between the DBM particles and reduce the distance for cells (e.g., osteoclasts, osteoblasts, etc.) to travel throughout the device to allow those cells to receive an adequate osteoinductive signal as opposed to only along the surface of the device. In some embodiment, the device improves the fusion of adjacent interspinous processes.

According to one aspect, there is a bone graft delivery device comprising: a porous biodegradable graft body for inducing bone growth at a surgical site, the porous biodegradable graft body having demineralized bone matrix (DBM) fibers disposed within the porous biodegradable body, and DBM powder disposed adjacent to, on or in the DBM fibers, wherein the porous biodegradable graft body facilitates transfer of cells into and out of the porous biodegradable graft body to induce bone growth at the surgical site.

Bone Powder

In various embodiments, the bone may be particulated such as, for example, in bone powder or fiber form. If the bone is demineralized, the bone may be made into a particulate before, during or after demineralization. In some embodiments, the bone may be monolithic and may not be a particulate. Accordingly, while specific discussion is given to particulate, the methods disclosed herein and the nanoscale textured surfaces disclosed herein may be used with monolithic bones or implants, including, for example, surface demineralized implants or fully demineralized cortical bone implants.

The bone may be milled and ground or otherwise processed into particles of an appropriate size before or after demineralization. The particles may be particulate (e.g., powder) or fibrous. The terms milling or grinding are not intended to be limited to production of particles of a specific type and may refer to production of particulate or fibrous particles. In certain embodiments, the particle size may be greater than 25 microns, such as ranging from about 25 to about 2000 microns, or from about 25 to about 500 microns or from about 200 to about 1000 microns. In some embodiments, the size of the bone powder particles are less than 100 microns. In some embodiments, the size of the bone powder particles are less than 500 microns.

In some embodiments, the particle size of the particles may be 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, 1000, 1005, 1010, 1015, 1020, 1025, 1030, 1035, 1040, 1045, 1050, 1055, 1060, 1065, 1070, 1075, 1080, 1085, 1090, 1095, 1100, 1105, 1110, 1115, 1120, 1125, 1130, 1135, 1140, 1145, 1150, 1155, 1160, 1165, 1170, 1175, 1180, 1185, 1190, 1195, 1200, 1205, 1210, 1215, 1220, 1225, 1230, 1235, 1240, 1245, 1250, 1255, 1260, 1265, 1270, 1275, 1280, 1285, 1290, 1295, 1300, 1305, 1310, 1315, 1320, 1325, 1330, 1335, 1340, 1345, 1350, 1355, 1360, 1365, 1370, 1375, 1380, 1385, 1390, 1395, 1400, 1405, 1410, 1415, 1420, 1425, 1430, 1435, 1440, 1445, 1450, 1455, 1460, 1465, 1470, 1475, 1480, 1485, 1490, 1495, 1500, 1505, 1510, 1515, 1520, 1525, 1530, 1535, 1540, 1545, 1550, 1555, 1560, 1565, 1570, 1575, 1580, 1585, 1590, 1595, 1600, 1605, 1610, 1615, 1620, 1625, 1630, 1635, 1640, 1645, 1650, 1655, 1660, 1665, 1670, 1675, 1680, 1685, 1690, 1695, 1700, 1705, 1710, 1715, 1720, 1725, 1730, 1735, 1740, 1745, 1750, 1755, 1760, 1765, 1770, 1775, 1780, 1785, 1790, 1795, 1800, 1805, 1810, 1815, 1820, 1825, 1830, 1835, 1840, 1845, 1850, 1855, 1860, 1865, 1870, 1875, 1880, 1885, 1890, 1895, 1900, 1905, 1910, 1915, 1920, 1925, 1930, 1935, 1940, 1945, 1950, 1955, 1960, 1965, 1970, 1975, 1980, 1985, 1990, 1995 and/or 2000 microns. After grinding, the bone particles may be sieved to select those particles of a desired size. In certain embodiments, the particles may be sieved though a 25 micron sieve, a 50 micron sieve, a 75 micron sieve, a 100 micron sieve, a 125 micron sieve, a 150 micron sieve, a 175 micron sieve and/or a 200 micron sieve.

In some embodiments, the bone powder comprises DBM and/or mineralized bone. In some embodiments, the size of the bone powder particles is less than 25 microns. In some embodiments, the bone powder particle size is about 1, 2, 3, 4, 5, 6, 7, 8, 9, 10, 11, 12, 13, 14, 15, 16, 17, 18, 19, 20, 21, 22, 23 and/or 24 microns.

In various embodiments, the bone powder particles and/or the DBM and/or mineralized bone fibers have a sticky outer surface such that the bone powder can adhere to DBM and/or mineralized bone fibers. In various embodiments, the bone particles are naturally sticky. In some embodiments, an adhesive agent is applied to the bone powder and/or the bone fibers comprising a bio-adhesive, glue, cement, cyanoacrylate, silicones, hot melt adhesives and/or cellulosic binders. In various embodiments, the adhesive may be applied to the surface of the bone powder particles by spraying or brushing. In some embodiments, a charge is applied to the fibers and an opposite charge is applied to the bone powder, (i.e., the technique of electrostatic precipitation). The bone powder will be attracted to, and tenaciously adhere to, the surface of the fiber. Any of these application techniques can be repeated one or more times to build up a relatively thick layer of adherent bone powder on the surface of the fibers.

The bone powder can be applied directly to the DBM fiber and/or fully mineralized fiber and the mixture can be disposed in the porous biodegradable graft body. In some embodiments, the porous biodegradable graft body contains pores having a pore size from about 0.5 to about 2,000 microns. In some embodiments, the porous biodegradable graft body contains pores having a pore size of from about 0.5, 5, 50, 100, 150, 200, 250, 300, 350, 400, 450, 500, 550, 600, 650, 700, 750, 800, 850, 900, 950, 1,000, 1,050, 1,100, 1,150, 1,200, 1,250, 1,300, 1,350, 1,400, 1,450, 1,500, 1,550, 1,600, 1,650, 1,700, 1,750, 1,800, 1,850, 1,900, 1,950 to about 2,000 microns. In some embodiments, the pore size of the porous biodegradable graft body is uniform. In some embodiments, the pore size of the porous biodegradable graft body is non-uniform and includes various pore sizes in the range from 0.5 to about 2,000 microns. Alternatively, the DBM fiber, and DBM powder can be placed in a polymer (e.g., collagen) and inserted into the porous biodegradable graft body (e.g., a pouch, container, etc.).

Demineralized Bone Material

Following shaving, milling or other technique whereby they are obtained, the bone material is subjected to demineralization in order to reduce its inorganic content to a very low level, in some embodiments, to not more than about 5% by weight of residual calcium and preferably to not more than about 1% by weight residual calcium. Demineralization of the bone material ordinarily results in its contraction to some extent.

Bone used in the methods described herein may be autograft, allograft, or xenograft. In various embodiments, the bone may be cortical bone, cancellous bone, or cortico-cancellous bone. While specific discussion is made herein to demineralized bone matrix, bone matrix treated in accordance with the teachings herein may be non-demineralized, demineralized, partially demineralized, or surface demineralized. The following discussion applies to demineralized, partially demineralized, and surface demineralized bone matrix. In one embodiment, the demineralized bone is sourced from bovine or human bone. In another embodiment, demineralized bone is sourced from human bone. In one embodiment, the demineralized bone is sourced from the patient's own bone (autogenous bone). In another embodiment, the demineralized bone is sourced from a different animal (including a cadaver) of the same species (allograft bone).

Any suitable manner of demineralizing the bone may be used. Demineralization of the bone material can be conducted in accordance with known conventional procedures. For example, in a preferred demineralization procedure, the bone materials useful for the implantable composition of this application are subjected to an acid demineralization step that is followed by a defatting/disinfecting step. The bone material is immersed in acid over time to effect its demineralization. Acids which can be employed in this step include inorganic acids such as hydrochloric acid and organic acids such as peracetic acid, acetic acid, citric acid, or propionic acid. The depth of demineralization into the bone surface can be controlled by adjusting the treatment time, temperature of the demineralizing solution, concentration of the demineralizing solution, agitation intensity during treatment, and other applied forces such as vacuum, centrifuge, pressure, and other factors such as known to those skilled in the art. Thus, in various embodiments, the bone material may be fully demineralized, partially demineralized, or surface demineralized.

After acid treatment, the bone is rinsed with sterile water for injection, buffered with a buffering agent to a final predetermined pH and then finally rinsed with water for injection to remove residual amounts of acid and buffering agent or washed with water to remove residual acid and thereby raise the pH. Following demineralization, the bone material is immersed in solution to effect its defatting. A preferred defatting/disinfectant solution is an aqueous solution of ethanol, the ethanol being a good solvent for lipids and the water being a good hydrophilic carrier to enable the solution to penetrate more deeply into the bone. The aqueous ethanol solution also disinfects the bone by killing vegetative microorganisms and viruses. Ordinarily at least about 10 to 40 weight percent by weight of water (i.e., about 60 to 90 weight percent of defatting agent such as alcohol) should be present in the defatting/disinfecting solution to produce optimal lipid removal and disinfection within the shortest period of time. The preferred concentration range of the defatting solution is from about 60 to 85 weight percent alcohol and most preferably about 70 weight percent alcohol.

Further in accordance with this application, the DBM material can be used immediately for preparation of the implant composition or it can be stored under aseptic conditions, advantageously in a critical point dried state prior to such preparation. In a preferred embodiment, the bone material can retain some of its original mineral content such that the composition is rendered capable of being imaged utilizing radiographic techniques.

In various embodiments, this application also provides bone matrix compositions comprising critical point drying (CPD) fibers. DBM includes the collagen matrix of the bone together with acid insoluble proteins including bone morphogenic proteins (BMPs) and other growth factors. It can be formulated for use as granules, gels, sponge material or putty and can be freeze-dried for storage. Sterilization procedures used to protect from disease transmission may reduce the activity of beneficial growth factors in the DBM. DBM provides an initial osteoconductive matrix and exhibits a degree of osteoinductive potential, inducing the infiltration and differentiation of osteoprogenitor cells from the surrounding tissues.

DBM preparations have been used for many years in orthopedic medicine to promote the formation of bone. For example, DBM has found use in the repair of fractures, in the fusion of vertebrae, in joint replacement surgery, and in treating bone destruction due to underlying disease such as rheumatoid arthritis. DBM is thought to promote bone formation in vivo by osteoconductive and osteoinductive processes. The osteoinductive effect of implanted DBM compositions is thought to result from the presence of active growth factors present on the isolated collagen-based matrix. These factors include members of the TGF-β, IGF, and BMP protein families. Particular examples of osteoinductive factors include TGF-β, IGF-1, IGF-2, BMP-2, BMP-7, parathyroid hormone (PTH), and angiogenic factors. Other osteoinductive factors such as osteocalcin and osteopontin are also likely to be present in DBM preparations as well. There are also likely to be other unnamed or undiscovered osteoinductive factors present in DBM.

In various embodiments, the DBM provided in the methods described in this application is prepared from elongated bone fibers which have been subjected to critical point drying. The elongated CPD bone fibers employed in this application are generally characterized as having relatively high average length to average width ratios, also known as the aspect ratio. In various embodiments, the aspect ratio of the elongated bone fibers is at least from about 50:1 to about at least about 1000:1. Such elongated bone fibers can be readily obtained by any one of several methods, for example, by milling or shaving the surface of an entire bone or relatively large section of bone.

In other embodiments, the length of the fibers can be at least about 3.5 cm and average width from about 20 mm to about 1 cm. In various embodiments, the average length of the elongated fibers can be from about 3.5 cm to about 6.0 cm and the average width from about 20 mm to about 1 cm. In other embodiments, the elongated fibers can have an average length be from about 4.0 cm to about 6.0 cm and an average width from about 20 mm to about 1 cm.

In yet other embodiments, the diameter or average width of the elongated fibers is, for example, not more than about 1.00 cm, not more than 0.5 cm or not more than about 0.01 cm. In still other embodiments, the diameter or average width of the fibers can be from about 0.01 cm to about 0.4 cm or from about 0.02 cm to about 0.3 cm.

In another embodiment, the aspect ratio of the fibers can be from about 50:1 to about 950:1, from about 50:1 to about 750:1, from about 50:1 to about 500:1, from about 50:1 to about 250:1; or from about 50:1 to about 100:1. Fibers according to this disclosure can advantageously have an aspect ratio from about 50:1 to about 1000:1, from about 50:1 to about 950:1, from about 50:1 to about 750:1, from about 50:1 to about 600:1, from about 50:1 to about 350:1, from about 50:1 to about 200:1, from about 50:1 to about 100:1, or from about 50:1 to about 75:1.

In some embodiments, the chips to fibers ratio is about 90:10, 80:20, 70:30, 60:40, 50:50, 40:60, 30:70, 20:80 and/or 10:90. In various embodiments, a surface demineralized chips to fibers ratio is about 90:10, 80:20, 70:30, 60:40, 50:50, 40:60, 30:70, 20:80 and/or 10:90. In some embodiments, a surface demineralized chips to fully demineralized fibers ratio is about 90:10, 80:20, 70:30, 60:40, 50:50, 40:60, 30:70, 20:80 and/or 10:90.

To prepare the osteogenic DBM, a quantity of fibers is combined with a biocompatible carrier to provide a demineralized bone matrix.

DBM typically is dried, for example via lyophilization or solvent drying, to store and maintain the DBM in active condition for implantation. Moreover, each of these processes is thought to reduce the overall surface area structure of bone. As may be appreciated, the structural damage of the exterior surface reduces the overall surface area. Physical alterations to the surface and reduction in surface area can affect cell attachment, mobility, proliferation, and differentiation. The surface's affinity for growth factors and release kinetics of growth factors from the surface may also be altered.

Accordingly, in some embodiments, methods for drying bone to store and maintain the bone in active condition for implantation that maintains or increases the surface area of the bone are provided. In one embodiment, the bone matrix is treated using critical point drying (CPD) technique, thereby reducing destruction of the surface of the bone. While specific description is made to critical point drying, it is to be appreciated that, in alternative embodiments, super critical point treatment may be used. In various embodiments utilizing CPD, a percentage of collagen fibrils on the surface of the bone are non-denatured after drying to a residual moisture content of approximately 15% or less. In some embodiments, after drying, the bone matrix has a residual moisture content of approximately 8% or less. In some embodiments, after drying, the bone matrix has a residual moisture content of approximately 6% or less. In some embodiments, after drying, the bone matrix has a residual moisture content of approximately 6% or less. In some embodiments, after drying, the bone matrix has a residual moisture content of approximately 3% or less.

Evaporative drying and freeze drying of specimens can cause deformation and collapse of surface structures, leading to a decrease in surface area. Without wishing to be bound to a particularly theory, this deformation and structure is thought to be caused because, as a substance crosses the boundary from liquid to gas, the substance volatilizes such that the volume of the liquid decreases. As this happens, surface tension at the solid-liquid interface pulls against any structures to which the liquid is attached. Delicate surface structures tend to be broken apart by this surface tension. Such damage may be caused by the effects of surface tension on the liquid/gas interface. Critical point drying is a technique that avoids effects of surface tension on the liquid/gas interface by substantially preventing a liquid/gas interface from developing. Critical point or supercritical drying does not cross any phase boundary, instead passing through the supercritical region, where the distinction between gas and liquid ceases to apply. As a result, materials dehydrated using critical point drying are not exposed to damaging surface tension forces. When the critical point of the liquid is reached, it is possible to pass from liquid to gas without abrupt change in state. Critical point drying can be used with bone matrices to phase change from liquid to dry gas without the effects of surface tension. Accordingly, bone dehydrated using critical point drying can retain or increase at least some of the surface structure and therefore the surface area.

In some embodiments, critical point drying is carried out using carbon dioxide. However, other mediums such as Freon, including Freon 13 (chlorotrifluoromethane), may be used. Generally, fluids suitable for supercritical drying include carbon dioxide (critical point 304.25 K at 7.39 MPa or $31.1°$ C. at 1072 psi or $31.2°$ C. and 73.8 bar) and Freon (about 300 K at 3.5-4 MPa or 25 to $30°$ C. at 500-600 psi). Nitrous oxide has similar physical behavior to carbon dioxide, but is a powerful oxidizer in its supercritical state. Supercritical water is also a powerful oxidizer, partly because its critical point occurs at such a high temperature ($374°$ C.) and pressure (3212 psi/647K and 22.064 MPa).

In some embodiments, the bone may be pretreated to remove water prior to critical point drying. Thus, in accordance with one embodiment, bone matrix is dried using carbon dioxide in (or above) its critical point status. After demineralization, bone matrix samples (in water) may be dehydrated to remove residual water content. Such dehydration may be, for example, through a series of graded ethanol solutions (for example, 20%, 50%, 70%, 80%, 90%, 95%, 100% ethanol in deionized water). In some embodiments, penetrating the tissue with a graded series of ethanol solutions or alcohols may be accomplished in an automated fashion. For example, pressure and vacuum could be used to accelerate penetration into the tissue.

In alternative embodiments, other means or procedures for removing water (drying or dehydrating) from the bone may be used. For example, the bone may be washed with other dehydrating liquids such as acetone to remove water, exploiting the complete miscibility of these two fluids. The acetone may then be washed away with high pressure liquid carbon dioxide.

In some embodiments, the dehydrated bone matrix is placed in a chamber within a critical point drying (CPD) apparatus and flushed with liquid $CO_2$ to remove ethanol (or other dehydrating liquid). Flushing with liquid $CO_2$ may be done one or more times. The temperature and/or pressure are then raised to the critical point (the critical point for $CO_2$ is reached at $31.2°$ C. and 73.8 bar). To perform critical point drying, the temperature and pressure may continue to be raised, for example to $40°$ C. with corresponding pressure of 85 bar. Thus, in some embodiments, the liquid carbon dioxide is heated until its pressure is at or above the critical point, at which time the pressure can be gradually released, allowing the gas to escape and leaving a dried product.

In certain embodiments, bone fibers processed using CPD have a BET surface area from about 1 to about 5 $m^2/gm$, a value 3 or 4 times greater than lyophilized bone fibers. In other embodiments, DBM fibers processed using CPD have a BET area surface from about 40 to about 100 m²/gm, a value 100 times greater than when DBM fibers are lyophilized.

In a further embodiment, the critical point dried samples may further be treated, or alternatively be treated, with supercritical carbon dioxide (carbon dioxide above the critical point). Supercritical $CO_2$ may also be useful in viral inactivation. In some embodiments, thus, the bone matrix is placed in a supercritical $CO_2$ chamber and liquid $CO_2$ is introduced, for example, by an air pump. The temperature is raised to 105° C. with corresponding pressure about 485 bar. In alternative embodiments, other temperatures and/or pressures above the critical point of $CO_2$ may be used. The samples are soaked in supercritical $CO_2$ for a certain time and $CO_2$ is released. The resulting bone samples retain surface morphologies, hence surface area, and osteoinductivity after such treatment.

In yet a further embodiment, monolithic bone is demineralized and particulated before drying. Accordingly, the bone may be demineralized in monolithic pieces. The demineralized monolithic pieces may then be milled in a wet condition and critical point dried, for example using carbon dioxide as a medium.

In yet a further embodiment, monolithic bone is demineralized and dried before particulating (if done). Accordingly, the bone may be demineralized in monolithic pieces. The DBM is pressed in a wet condition and then critical point dried, for example using carbon dioxide as a medium. In alternatives of this embodiment, the demineralized and dried monolithic bone is not particulated and is processed as a monolithic implant.

Bone Graft Device

FIG. 1 depicts a perspective view of an exemplary bone graft delivery device 100 according to an aspect of the present application. The bone graft delivery device may be formed in any shape, size or configuration to fit in a desired bone site and may include at least one attachment member in any location or orientation thereon. It is noted that the embodiments shown are for exemplary purposes only and alternate embodiments of the bone graft delivery device may be contemplated.

Figure 2:
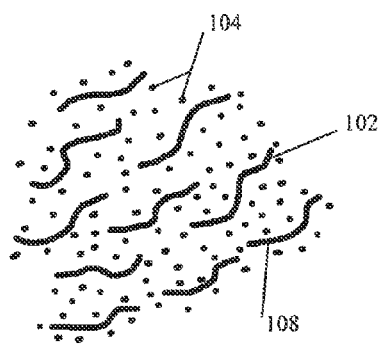
FIG. 2 depicts a top view of components of an exemplary bone graft delivery device according to an aspect of the present application.
Figure 3:
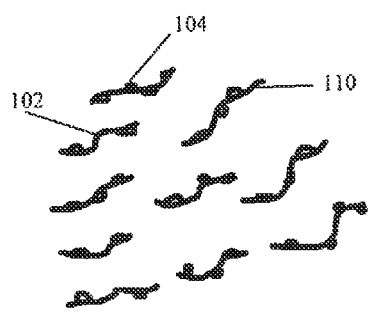
FIG. 3 depicts a top view of components of an exemplary bone graft delivery device according to an aspect of the present application.

In some embodiments, the bone graft delivery device comprises a porous biodegradable graft body 106 having demineralized bone matrix (DBM) fibers 102 disposed within the porous biodegradable graft body, and DBM powder 104 disposed adjacent to, on or in the DBM fibers, as shown in FIGS. 1 and 2. The porous biodegradable graft body facilitates transfer of cells into and out of the porous biodegradable graft body to induce bone growth at a surgical site. In some embodiments, the DBM powder is disposed on and adheres to the DBM fibers, as shown in FIG. 3. This can be accomplished by, for example, an adhesive or another polymer. Alternatively, the DBM fibers entangle the DBM powder and reduce the gap for cells to travel. In some embodiments, the DBM fibers and DBM powder can be disposed in a collagen matrix which can be slid into a porous biodegradable implant body.

In various embodiments, the bone graft material comprises mineralized bone fibers 108. In various embodiments, the DBM powder is disposed on the DBM fiber. In various embodiments, the DBM fiber and the DBM powder are disposed in a collagen matrix that is disposed in the porous biodegradable graft body. In some embodiments, DBM and mineralized bone fibers are dispersed throughout the porous biodegradable graft body.

In some embodiments, the DBM powder adheres to the DBM fibers and the mineralized bone fibers via a surface 110 located on the DBM fibers. The DBM powder adheres the DBM fibers so as to reduce and/or eliminate gaps that exist between the fibers. In some embodiments, the DBM powder adheres to the DBM fibers to improve osteoinductivity for facilitating bone fusion, for example, interspinous process fusion.

In various embodiments, the surface of the bone fiber is naturally sticky. In some embodiments, an adhesive agent is applied to the DBM powder and/or the DBM fibers comprising a bio-adhesive, glue, cement, cyanoacrylate, silicones, hot melt adhesives and/or cellulosic binders. Alternatively, the DBM fibers can entangle the bone powder.

In some embodiments, the DBM powder has a small particle size so as to improve osteoinductivity. In various embodiments, the DBM powder has a particle size of about 25 to about 500 microns. In some embodiments, the DBM powder has a small diameter so as to increase the DBM powders surface area and exposure of osteoinductive proteins. In some embodiments, the average length of the DBM fibers and the mineralized bone fibers are from about 0.25 cm to about 10 cm and the average length of the DBM fibers and the mineralized bone fibers are from about 0.15 cm to about 5 cm. In various embodiments, the average length of the DBM fibers and the mineralized bone fibers are from about 0.50 cm to about 3 cm.

In some embodiments, the DBM fibers have a thickness of about 0.5-4 mm. In various embodiments, the DBM fibers have a thickness of about 0.5, 0.6, 0.7, 0.8, 0.9, 1, 1.5, 2, 2.5, 3, 3.5 and/or 4 mm. In various embodiments, the ratio of DBM fibers to DBM powder is about 40:60 to about 90:10 W/W, W/V or V/V. In some embodiments, the ratio of mineralized bone fibers to DBM powder is about 25:75 to about 75:25 W/W, W/V or V/V. In various embodiments, the device comprises DBM fibers and mineralized fibers in a ratio of 40:60 to about 90:10 W/W, W/V or V/V. In some embodiments, the DBM fibers to DBM powder ratio, mineralized bone fibers to DBM powder ratio and/or the DBM fibers and mineralized fibers ratio is from 5:95 to about 95:5 W/W, W/V or V/V. In some embodiments, the DBM fibers to DBM powder ratio, mineralized bone fibers to DBM powder ratio and/or the DBM fibers and mineralized fibers ratio is 5:95, 10:90, 15:85, 20:80, 25:75, 30:70, 35:65, 40:60, 45:55, 50:50, 55:45, 60:40, 65:35, 70:30, 75:25, 80:20, 85:15, 90:10 and/or 95:5 W/W, W/V or V/V.

Figure 4:
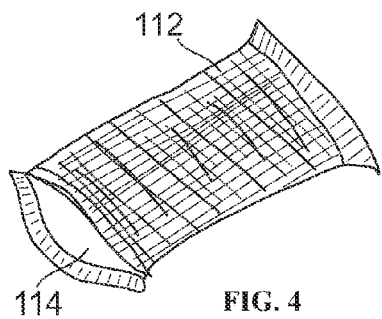
FIG. 4 depicts a perspective view of an exemplary bone graft delivery device, according to an aspect of the present application.

In some embodiments, the porous biodegradable graft body is shaped as an insert 112, as shown in FIG. 4. A sealable opening 114 is disposed at an end of the insert to facilitate disposal of the graft material within the insert. In some embodiments, the graft material comprises demineralized bone material comprising demineralized bone, fibers, powder, chips, triangular prisms, spheres, cubes, cylinders, shards or other shapes having irregular or random geometries. These can include, for example, "substantially demineralized," "partially demineralized," or "fully demineralized" cortical and/or cancellous bone. These also include surface demineralization, where the surface of the bone construct is substantially demineralized, partially demineralized, or fully demineralized, yet the body of the bone construct is fully mineralized.

In various embodiments, the bone graft material comprises fully DBM fibers and surface demineralized bone chips. In some embodiments, the ratio of fully DBM fibers to surface demineralized bone chips is from 5:95 to about 95:5 fibers to chips. In some embodiments, the ratio of fully DBM fibers to surface demineralized bone chips is 5:95, 10:90, 15:85, 20:80, 25:75, 30:70, 35:65, 40:60, 45:55, 50:50, 55:45, 60:40, 65:35, 70:30, 75:25, 80:20, 85:15, 90:10 and/or 95:5 fibers to chips. In various embodiments, the fully DBM fibers have a thickness of about 0.5-4 mm. In various embodiments, the fully DBM fibers have a thickness of about 0.5, 0.6, 0.7, 0.8, 0.9, 1, 1.5, 2, 2.5, 3, 3.5 and/or 4 mm.

In some embodiments the porous biodegradable graft body comprises a mesh sealed bag comprising pores at about 100 to about 200 microns. In various embodiments, the porous biodegradable graft body comprises a mesh sealed bag comprising natural materials, synthetic polymeric resorbable materials, synthetic polymeric non-resorbable materials or other materials. In some embodiments, the porous biodegradable graft body comprises a mesh sealed bag comprising human skin, collagen, human hair, polyethylene glycol, chitosan, alginate, cellulose, hyaluronic acid, keratin, a biodegradable polymer, poly(lactide-co-glycolide), fat, bone, or a combination thereof. In various embodiments, the mesh sealed bag is sealed via heat sealing, stitching, adhesion, tying, fold lock and cinching.

In some embodiments, the bone graft delivery device comprises a polymer (e.g., collagen) matrix. The DBM fibers and the DBM powder are suspended in the polymer matrix, and the polymer matrix is disposed within the porous biodegradable graft body for placement at a surgical site to facilitate transfer of cells into and out of the porous biodegradable graft body to induce bone growth at the surgical site. In various embodiments, the bone graft delivery device further comprises mineralized bone fibers suspended in the polymer matrix. In some embodiments, the DBM powder is suspended in the polymer matrix between the DBM fibers and the mineralized bone fibers. In some embodiments, the DBM powder is suspended between the DBM fibers in the polymer matrix so as to reduce and/or eliminate gaps that exist between the fibers. In some embodiments, the DBM powder is suspended between the DBM fibers in the polymer matrix to improve osteoinductivity for facilitating bone fusion, for example, interspinous process fusion.

In various embodiments, the polymer matrix is a porous sponge and comprises natural polymers comprising collagen, chitosan, alginate or hyaluronic acid. In some embodiments, the porous sponge comprises other natural polymers such as, for example, gelatin.

In some embodiments, the polymer matrix comprises a bioerodible, a bioabsorbable, and/or a biodegradable biopolymer that may provide immediate release, or sustained release. Examples of suitable sustained release biopolymers include but are not limited to poly(alpha-hydroxy acids), poly(lactide-co-glycolide) (PLGA), polylactide (PLA), polyglycolide (PG), polyethylene glycol (PEG) conjugates of poly(alpha-hydroxy acids), poly(orthoester)s (POE), polyaspirins, polyphosphagenes, collagen, starch, pre-gelatinized starch, hyaluronic acid, chitosans, gelatin, alginates, albumin, fibrin, vitamin E compounds, such as alpha tocopheryl acetate, d-alpha tocopheryl succinate, D,L-lactide, or L-lactide, caprolactone, dextrans, vinylpyrrolidone, polyvinyl alcohol (PVA), PVA-g-PLGA, PEGT-PBT copolymer (polyactive), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) or combinations thereof. As persons of ordinary skill are aware, mPEG and/or PEG may be used as a plasticizer for PLGA, but other polymers/excipients may be used to achieve the same effect. mPEG imparts malleability to the polymer. In some embodiments, these biopolymers may also be coated on the medical device to provide the desired release profile. In some embodiments, the coating thickness may be thin, for example, from about 5, 10, 15, 20, 25, 30, 35, 40, 45 or 50 microns to thicker coatings 60, 65, 70, 75, 80, 85, 90, 95, 100 microns to delay release of the substance from the medical device. In some embodiments, the range of the coating on the bone graft delivery device ranges from about 5 microns to about 250 microns or 5 microns to about 200 microns to delay release from the bone graft delivery device.

In various embodiments, various components of the bone graft delivery device comprises poly(lactide-co-glycolide) (PLGA), polylactide (PLA), polyglycolide (PGA), D-lactide, D,L-lactide, L-lactide, D,L-lactide-co-ε-caprolactone, D,L-lactide-co-glycolide-co-ε-caprolactone, L-lactide-co-ε-caprolactone or a combination thereof.

In some embodiments, the bone graft delivery device further comprises bone morphogenic proteins (BMPs), growth factors, antibiotics, angiogenesis promoting materials, bioactive agents or other actively releasing materials.

In various embodiments, the fibers and/or the powder is surface DBM. In some embodiments, the fibers and/or the powder is surface DBM cortical allograft. In various embodiments, surface demineralization involves surface demineralization to at least a certain depth. For example, the surface demineralization of the of the allograft can be from about 0.25 mm, 0.5 mm, 1 mm, 1.5 mm, 2.0 mm, 2.5 mm, 3.0 mm. 3.5 mm, 4 mm, 4.5 mm, to about 5 mm. The edges of the bone fibers and/or powder may further be machined into any shape or to include features such as grooves, protrusions, indentations, etc., to help improve fit and limit any movement or micromotion to help fusion and/or osteoinduction to occur.

In some embodiments, the bone graft body may be shaped or formed to fit between two adjacent spinous processes. In some embodiments, the bone graft body may be shaped as a biodegradable mesh bag or a block having ridges, teeth, threads, wedges, bumps, cylinders, pyramids, blocks, valleys, dimples, holes, grids, mortises, tenons, tongues, grooves, valleys, troughs, dimples, pits, dovetails or a combination thereof to reduce or prevent movement of the biodegradable mesh bag or block.

Generally, the porous biodegradable graft body may be a single or multi-compartment structure capable of at least partially retaining a substance provided therein until the porous biodegradable graft body is placed at a surgical site. Upon placement, the porous biodegradable graft body facilitates transfer of the substance and/or materials surrounding the surgical site. The porous biodegradable graft body may participate in, control, or otherwise adjust, the release of the substance or penetration of the porous biodegradable graft body by surrounding materials, such as cells or tissues.

In some embodiments, the porous biodegradable graft body comprises natural and synthetic polymers, which provide and extended and/or increased shelf life, preferably of over at least six months. The extended shelf life of the polymers prevents environmental degradation of the porous biodegradable graft body, thus increasing efficiency, preventing waste and providing a more effective, usable product over an extended period of time.

In various embodiments, the porous biodegradable graft body may further provide moisture and radiation resistance to improve stability during sterilization procedures. For example, the polymers utilized in the porous biodegradable graft body can impart increased moisture resistance to protect premature biodegradation of the porous biodegradable graft body, and thus preserve the delivery device contents. Further, the polymers preferably utilized in the porous biodegradable graft body can provide increased resistance and durability to radiation, such as radiation exposure during sterilization procedures.

In some embodiments, the graft body may comprise a mesh material. In some embodiments, the graft body is a biodegradable mesh bag. Suitable mesh materials include natural materials, synthetic polymeric resorbable materials, synthetic polymeric non-resorbable materials, and other materials. Natural mesh materials include silk, extracellular matrix (such as DBM, collagen, ligament, tendon tissue, or other), silk-elastin, elastin, collagen, and cellulose. Synthetic polymeric resorbable materials include poly(lactic acid) (PLA), poly(glycolic acid) (PGA), poly(lactic acid-glycolic acid) (PLGA), polydioxanone, PVA, polyurethanes, polycarbonates, and others. Other suitable materials include carbon fiber, metal fiber, and various meshes. In other embodiments, the graft body may comprise non-woven material such as spun cocoon or shape memory materials having a coil shape or shape memory alloys.

Generally, the graft body may be formed of any natural or synthetic structure (tissue, protein, carbohydrate) that can be used to form a graft body configuration. Thus, the graft body may be formed of a polymer (such as polyalkylenes (e.g., polyethylenes, polypropylenes, etc.), polyamides, polyesters, poly(glaxanone), poly(orthoesters), poly(pyrolicacid), poly (phosphazenes), polycarbonate, other bioabsorbable polymer such as Dacron or other known surgical plastics, a natural biologically derived material such as collagen, gelatin, chitosan, alginate, a ceramic (with bone-growth enhancers, hydroxyapatite, etc.), PEEK (polyether-etherketone), dessicated biodegradable material, metal, composite materials, a biocompatible textile (e.g., cotton, silk, linen), extracellular matrix components, tissues, or composites of synthetic and natural materials, or other. Various collagen materials can be used, alone or in combination with other materials, including collagen sutures and threads. Any suitable collagen material may be used, including known collagen materials, or collagen materials as disclosed in U.S. patent application Ser. No. 12/030,181, filed Feb. 12, 2008, hereby incorporated by reference in its entirety, which discloses collagen materials that may be used for forming a graft body. Some examples include polymer or collagen threads woven, or knitted into a mesh. Other suitable materials include thin polymer sheets molded in the presence of a porogen and having underwent leaching; polymer sheets or naturally derived sheets such as fascia and other collagen materials, small intestinal submucosa, or urinary bladder epithelium, the sheets being punctured to introduce porosity; specific shapes printed using available or future printing technologies; naturally secreted materials such as bacterial cellulose grown within specific molds; etc. In some embodiments, the polymer matrix containing the DBM fibers and bone powder can also contain a pore forming agent to enhance pores so that cells can travel in and out of the polymer matrix.

In some embodiments, in addition to the polymer matrix, the mesh fibers may be treated to impart porosity to the fibers. This may be done, for example, to PLA, PLGA, PGA, and other fibers. One suitable method for treating the mesh fibers comprises supercritical carbon dioxide treatment to partially solubilize the particles. This treatment may further be carried out for viral inactivation. Another suitable method for treating the mesh fibers comprises explosive decompression. Explosive decompression generates porosity and leads to controlled permeability. The mesh material further may be loaded with cells, growth factors, or bioactive agents.

In further embodiments, fibers of a mesh material may be treated such as by having particles adhered thereto. The particles may be, for example, bone particles. Thus, in one embodiment, the graft body may comprise a plurality of threads formed into a fabric. The threads may have particles adhered thereto. For example, the threads may have particles strung on the thread. In an alternative embodiment, the graft body may be formed of a material and the material may be coated with particles.

In yet other embodiments, the graft body may comprise a non-porous material, which may be permeable. A non-porous material may be used for later (or delayed) delivery of a substance provided therein. Such substance may comprise, for example, cells, growth factors, or bone morphogenetic proteins. Accordingly, in one embodiment, a delivery device for delayed delivery of cells, growth factors, or bone morphogenetic proteins is provided comprising a non-porous graft body.

The porous biodegradable graft body material may have functional characteristics. Alternatively, other materials having functional characteristics may be incorporated into the porous biodegradable graft body. Functional characteristics may include radiopacity, bacteriocidity, source for released materials, tackiness, etc. Such characteristics may be imparted substantially throughout the porous biodegradable graft body or at only certain positions or portions of the porous biodegradable graft body.

Suitable radiopaque materials include, for example, ceramics, mineralized bone, ceramics/calcium phosphates/calcium sulfates, metal particles, fibers, and iodinated polymer (see, for example, WO/2007/143698). Polymeric materials may be used to form the porous biodegradable graft body and be made radiopaque by iodinating them, such as taught for example in U.S. Pat. No. 6,585,755, herein incorporated by reference in its entirety. Other techniques for incorporating a biocompatible metal or metal salt into a polymer to increase radiopacity of the polymer may also be used. Suitable bacteriocidal materials may include, for example, trace metallic elements. In some embodiments, trace metallic elements may also encourage bone growth.

Functional material, such as radiopaque markers, may be provided at one or more locations on the porous biodegradable graft body or may be provided substantially throughout the porous biodegradable graft body. Thus, for example, in a tubular graft body, a radiopaque marker may be provided at a tip of the tubular graft body. Such marker may facilitate placement of the graft body. Radiopaque materials may be incorporated into the graft body and/or into the substance for delivery by the graft body. Further, radiopaque materials may be provided at only some locations on the graft body such that visualization of those locations provides indication of the orientation of the graft body in vivo.

The graft body itself may be designed to release materials during degradation of the graft body material. Thus, bone morphogenic proteins (BMPs), growth factors, antibiotics, angiogenesis promoting materials (discussed more fully below), bioactive agents (discussed more fully below), or other actively releasing materials may be incorporated into the graft body material such that as the graft body material is degraded in the body, the actively releasing material is released. For example, an actively releasing material may be incorporated into a biodegradable polymer graft body such as one manufactured of a biodegradable polyester such as poly (lactic acid) (PLA), poly(glycolic acid) (PGA), poly(lactic-co-glycolic acid) (PLGA), or polyhydroxyalkanoates (polyhydroxybutyrates and polyhydroxyvalerates and copolymers). In some embodiments, poly(ethylene glycol) (PEG) may be incorporated into the biodegradable polyester to add hydrophilic and other physico-chemical properties to enhance drug delivery. In some embodiments, composites of allograft bone and biodegradable polymers (for example, PLEXUR® products available from Osteotech) may be used in the graft body.

In some embodiments, the graft body may comprise a material that becomes tacky upon wetting. Such material may be, for example, a protein or gelatin based material. Tissue adhesives, including mussel adhesive proteins and cryanocrylates, may be used to impart tackiness to the graft body. In further examples, alginate or chitosan material may be used to impart tackiness to the graft body. In further embodiments, an adhesive substance or material may be placed on a portion of the graft body or in a particular region of the graft body to anchor that portion or region of the graft body in place at an implant site.

In one embodiment of a graft body comprising two compartments, first and second materials may be used for the first and second compartments, respectively. The first material may release or expose a growth factor according to a first rate and the second material may release a growth factor according to a second rate. Further, the growth factors released by the first and second compartments may be the same or may be different. For example, an angiogenic growth factor may be provided with the first compartment and an osteoinductive growth factor may be provided with the second compartment.

Mesh Formulations

Any suitable technique may be used for forming a material for the graft body. Generally, the material may be formed as a substantially solid material, as a sheet, as a mesh, or in other configurations. In some embodiments, the material may be a textile type material. Thus, for example, the material may be formed using a textile approach such as be weaving, rug making, knitting, etc. Such formation may be by a mechanical or industrial method. In another embodiment, a substantially solid sheet may be formed and may be treated to assume a configuration penetrable by cells, fluids, and proteins. For example, the sheet may be perforated, may be expanded to create openings, or other. Also, it would be perfectly suitable to take a thin sheet of the graft body material, and to perforate it, expand it to create openings, or otherwise make it penetrable by cells, fluids and proteins.

In one embodiment, elongated bone-derived particles or fragments of small intestinal submucosa (for example, approximately 6) may be combined longitudinally into three small bundles, each having, for example, from about 1 to about 3 tissue particles. The three bundles may then be braided. Various methods of braiding and types of braids any of which may be useful in producing the material of the application herein are also described. The ends of the braided tissue-derived particles may then be glued together using a fixation agent to prevent their unraveling, or they may be held together with a biocompatible polymer or metal band.

In an alternative embodiment, bone-derived particles are combined with a solvent to form a material. Exemplary solvents include water, lower alkanols, ketones, and ethers and mixtures of any of these or other materials. The material may then be extruded at an appropriate temperature and pressure to create a thread. Threads may also be produced by spinning, drawing, rolling, solvent-extruding, cutting or laser cutting from a sheet or bar stock. The material may alternatively be cast or molded into a solid sheet or bar stock and then cut into thin threads. These may be used immediately or woven into a mesh. Alternatively or in addition, they may be spliced, wrapped, plied, cabled, braided, woven, or some combination of these. The material may be shaped by thermal or chemical bonding, or both. In one embodiment, a portion of the solvent is removed from the material before extrusion.

Alternatively or in addition, the material may be cast as a slurry, extruded, or molded. A variety of materials processing methods will be well known to those skilled in the art. For example, the material may be solvent cast using a press such as a Carver press to spread the material into a film. Solvent evaporation will yield a porous film. Alternatively, the material may be compression molded into a film. The mesh size or porosity of the film will depend on the thickness of the film and the viscosity of the precursor and can be easily manipulated by one skilled in the art. Where elongated particles are used in an extruded aggregate, they will tend to be aligned roughly parallel to one another.

In an alternative embodiment, a thread of a biocompatible natural or synthetic material, for example, polylactide or collagen, may be coated with tissue-derived or other elements, for example, by dubbing. For example, a polymer fiber may be coated with an adhesive, for example, lecithin, and bone particles or other osteoconductive or osteoinductive fibrils allowed to adhere to the thread. The thread may then be twisted on itself or with a second or a plurality of similarly treated threads. Alternatively or in addition, the threads may be braided. The adhesive may be a lipid that is waxy at room temperature, for example, a di- or tri-glyceride that is solid at room temperature. Alternatively or in addition, the adhesive may be a phosphocholine or phosphatidylcholine. In some embodiments, the adhesive is a material that binds both the thread and the material that is used to coat the thread (e.g., bone particles) but that does not degrade either. Non-aqueous adhesives may improve the stability of the final aggregate as compared to aqueous adhesives.

Suitable fibers may be formed utilizing well known techniques, e.g., braiding, plying, knitting, weaving, felting, that are applied to processing natural fibers, e.g., cotton, silk, etc., and synthetic fibers made from synthetic bioabsorbable polymers, e.g., poly(glycolide) and poly(lactic acid), nylon, cellulose acetate, etc. Specifically, collagen thread is wound onto cylindrical stainless steel spools. The spools are then mounted onto the braiding carousel, and the collagen thread is then assembled in accordance with the instructions provided with the braiding machine. In one particular run, a braid was formed of four collagen threads, which consisted of two threads of noncrosslinked collagen and two threads of crosslinked collagen. One skilled in the art will recognize that these techniques may be applied to the other fibrous materials described herein.

Fibers and more evenly dimensioned particles may also be plied into yarns using the same methods and same machinery known to those skilled in the art in plying threads made out of other material, e.g., cotton, polyester, etc.

Elongated materials including multistranded materials, e.g., braids, plied yams, cables, etc., may be knitted into tubular or flat fabrics by using techniques known to those skilled in the art of producing fabrics manufactured from other types of threads. Various biologically active substances can be incorporated in, or associated with, the braided, knitted, or woven materials. Particles and fibers and materials of these (including multistranded materials) may alternatively or additionally be assembled into a material by non-woven methods such as laying, needle-punching, and hooking (as for a rug). For example, a thread may be attached to another thread or a pressed film.

Regardless of the assembly method, the material shape, mesh size, cable thickness, and other structural characteristics, e.g., architecture, may be customized for the desired application. For example, where a two dimensional aggregate is used to retain a thixotropic material within a gap, a tight weave is preferred to prevent leakage. To optimize cell or fluid migration through the mesh, the pore size may be optimized for the viscosity and surface tension of the fluid or the size of the cells. For example, pore sizes on the order of approximately 100-200 µm may be used if cells are to migrate through the mesh. Mesh size may be controlled by physically weaving strands of the material by controlling the ratio of solvent to solids in a precursor material.

Cells may be seeded onto the material, or contained within it. In one embodiment, cells may be encapsulated in a matrix such as alginate or collagen gel and the capsules placed on the material. Seeded materials generally do not need to be incubated for long periods of time in solutions that could partially dissolve the binding agent. Instead, the capsules may be placed on the material or graft body shortly before implantation. In another embodiment, cells are simply mixed with a gel, which is then combined with the material. Alternatively, a material or graft body may be cultured with cells before implantation. In one embodiment, thicker materials are used for culturing to increase mechanical integrity during implantation. Any class of cells, including connective tissue cells, organ cells, muscle cells, nerve cells, and stem cells, may be seeded onto the implant. In an exemplary embodiment, connective tissue cells such as osteoblasts, osteoclasts, fibroblasts, tenocytes, chondrocytes, and ligament cells and partially differentiated stem cells such as mesenchymal stem cells and bone marrow stromal cells are employed.

As previously discussed, the graft body may be formed of as a mesh. Thus, the graft body may comprise a woven material. The woven material may have varying degrees of permeability. It may be permeable, semi-permeable, or non-permeable. Permeability may be with respect to cells, to liquids, to proteins, to growth factors, to bone morphogenetic proteins, or other. In further embodiments, the material may be braided.

In alternative embodiments, the graft body may comprise a substantially solid structure, such as a polymer structure with a chamber, or a spun cocoon.

The graft body may have any suitable configuration. For example, the graft body may be formed as a ring, a cylinder, a cage, a rectangular shape, a mesh, a suture-like wrap, a continuous tube, or other configuration. In specific embodiments, the graft body may be formed as a thin tube designed to be inserted through catheters or an introducer tube, a rectangular shape designed to fit adjacent to spinal processes for posterolateral spine fusion, a cube like structure designed to fit between vertebral bodies or within cages for interbody spinal fusion, a tube-like shape where the ends are designed to be fitted onto nonunion long bone defects, relatively flat shapes designed to fill cranial or maxillofacial defects, rectangular structures designed for osteochondral defects, structures preshaped to fit around various implants (e.g. dental, doughnut with hole for dental implants), or relatively elastic ring-like structures that will stretch and then conform to shapes (e.g. rubber band fitted around processes). In an embodiment wherein the graft body is formed as a cage, the cage may comprise a plurality of crossed filaments, which define between them a series of openings for tissue ingrowth. Any of these shapes may be used for a graft body comprising a plurality of compartments. For example, in a tubular embodiment, the tube may be formed into a plurality of compartments by tying a cord around the tube at one or more points, or by other suitable mechanism such as crimping, twisting, knotting, stapling, sewing, or other. The configuration of the graft body may be determined by the substance to be provided within the graft body. For example, if the substance to be contained comprises fibers, the graft body may be formed as strings or sutures that are wrapped around the fibers.

In certain embodiments, a bone void can be filled. A compartment within the graft body material can be at least partially filled with a bone repair substance. In various embodiments, at least partially filled as used herein, can mean that a percentage of the volume of a compartment (or graft body material, as applicable) is at least 70% occupied, at least 75% occupied, at least 80% occupied, at least 85% occupied, at least 90% occupied, at least 95% occupied, or 100% occupied. The graft body material can be inserted into an opening in the defect until the defect is substantially filled. In various embodiments, a substantially filled as used herein can mean that a percentage of the volume of a defect (or graft body material, as applicable) is at least 70% occupied, at least 75% occupied, at least 80% occupied, at least 85% occupied, at least 90% occupied, at least 95% occupied, or 100% occupied. The excess material extending beyond the surface of the bone if the bone were without the defect can then be removed, or at least partially removed such that the opening of the defect is flush with the uninjured bone surface.

In some embodiments, the graft body may be labeled. Such labeling may be done in any suitable manner and at any suitable location on the graft body. In some embodiments, labeling may be done by using a silk screen printing, using an altered weaving or knotting pattern, by using different colored threads, or other. The labeling may indicate information regarding the graft body. Such information might include part number, donor id number, number, lettering or wording indicating order of use in the procedure or implant size, etc.

In one embodiment, the graft body may comprise a penetrable material at a first compartment configured for placement adjacent bone and a substantially impenetrable material at a second compartment configured for placement adjacent soft tissue. Alternatively, the material of the compartments may have substantially identical characteristics. The graft body then can be positioned in any desirable manner. By way of example only, a graft body may have a porous surface that is positioned adjacent bone, and a separate or opposite surface that has a generally impenetrable surface that is positioned adjacent soft tissue. Alternatively, a graft body may have one compartment that comprises a porous material, and a second compartment that comprises a substantially impenetrable material.

For both single and multi-compartment graft bodies, the graft body may be closed after filling substances. Accordingly, the graft body may be provided in an unfilled, unsealed state. After a substance for delivery is placed in the graft body, the graft body may be permanently or temporarily closed. Permanent closure may be, for example, by heat sealing, stitching, adhesion, or other methods. Temporary closure may be by tying, fold lock, cinching, and etc. A temporarily closed graft body can be opened without damaging the graft body during surgical implantation to add or remove substances in the graft body.

In some embodiments, the bone graft delivery device may comprise two bone delivery devices.

Suitable adhesives for use may include, for example, cyanoacrylates (such as histoacryl, B Braun, which is n-Butyl-2 Cyanoacrylate; or Dermabond, which is 2-octylcyanoacrylate); epoxy-based compounds, dental resin sealants, dental resin cements, glass ionomer cements, polymethyl methacrylate, gelatin-resorcinol-formaldehyde glues, collagen-based glues, inorganic bonding agents such as zinc phosphate, magnesium phosphate or other phosphate-based cements, zinc carboxylate, L-DOPA (3,4-dihydroxy-L-phenylalanine), proteins, carbohydrates, glycoproteins, mucopolysaccharides, other polysaccharides, hydrogels, protein-based binders such as fibrin glues and mussel-derived adhesive proteins, and any other suitable substance. Adhesives may be selected for use based on their bonding time; e.g., in some circumstances, a temporary adhesive may be desirable, e.g., for fixation during the surgical procedure and for a limited time thereafter, while in other circumstances a permanent adhesive may be desired. Where the compartment is made of a material that is resorbable, the adhesive can be selected that would adhere for about as long as the material is present in the body. In some embodiments, the graft body material may be treated to form chemical linkages between the graft body and adjacent tissue, whether bone or soft tissue.

In some embodiments, biological attachment may be via mechanisms that promote tissue ingrowth such as by a porous coating or a hydroxyapatite-tricalcium phosphate (HA/TCP) coating. Generally, hydroxyapatite bonds by biological effects of new tissue formation. Porous ingrowth surfaces, such as titanium alloy materials in a beaded coating or tantalum porous metal or trabecular metal may be used and facilitate attachment at least by encouraging bone to grow through the porous implant surface. These mechanisms may be referred to as biological attachment mechanisms.

In some embodiments, the graft body can comprise edges having polymers that are more hydrophilic than the polymers in other areas of the graft body (e.g., body). In this embodiment, the graft body, when implanted, will draw bodily fluid to this area more so than in other areas and this will cause the edges of the graft body to expand and anchor the graft body at, near or in the defect site. Alternatively, the body of the graft body can have polymers that are more hydrophilic than the polymers in the edges of the graft body. In this embodiment, the graft body, when implanted, will draw bodily fluid to the body area more so than the edges and this will cause the body of the graft body to expand and anchor the graft body at, near or in the defect site.

Bioactive Agents

A substance is provided inside the graft body, before or during surgery (as described below), for delivery in vivo. Generally, the substance or material may be homogenous or heterogeneous. The substance or material may be selected to exhibit certain gradients. For example, the substance or material may be selected to exhibit a gradient to guide, lure, or attract cells along a pathway. Such gradient may comprise a cell gradient, a cell type gradient (for example transitioning from bone cells to cartilage cells or transitioning from bone cells to tendon cells), a gradient of conductivity, or a gradient of density/porosity. In some embodiments, the substance or material may comprise a sequence of ingredients.

The graft body may be used to deliver a substance comprising any suitable biocompatible material. In specific embodiments, the graft body may be used to deliver surface demineralized bone chips, optionally of a predetermined particle size, demineralized bone fibers, optionally pressed, and/or allograft. For embodiments wherein the substance is biologic, the substance may be autogenic, allogenic, xenogenic, or transgenic. Other suitable materials that may be positioned in the graft body include, for example, protein, nucleic acid, carbohydrate, lipids, collagen, allograft bone, autograft bone, cartilage stimulating substances, allograft cartilage, TCP, hydroxyapatite, calcium sulfate, polymer, nanofibrous polymers, growth factors, carriers for growth factors, growth factor extracts of tissues, DBM, dentine, bone marrow aspirate, bone marrow aspirate combined with various osteoinductive or osteoconductive carriers, concentrates of lipid derived or marrow derived adult stem cells, umbilical cord derived stem cells, adult or embryonic stem cells combined with various osteoinductive or osteoconductive carriers, transfected cell lines, bone forming cells derived from periosteum, combinations of bone stimulating and cartilage stimulating materials, committed or partially committed cells from the osteogenic or chondrogenic lineage, or combinations of any of the above. In some embodiments, the substance may be pressed before placement in the graft body. A substance provided within the graft body may be homogenous, or generally a single substance, or may be heterogeneous, or a mixture of substances.

In some embodiments, the graft body can comprise one or more compartments having demineralized bone material therein. The demineralized bone material can be comprise demineralized bone, powder, chips, triangular prisms, spheres, cubes, cylinders, shards, fibers or other shapes having irregular or random geometries. These can include, for example, "substantially demineralized," "partially demineralized," or "fully demineralized" cortical and cancellous bone. These also include surface demineralization, where the surface of the bone construct is substantially demineralized, partially demineralized, or fully demineralized, yet the body of the bone construct is fully mineralized. In some embodiments, the graft body may comprise some fully mineralized bone material. The configuration of the bone material can be obtained by milling, shaving, cutting or machining whole bone as described in for example U.S. Pat. No. 5,899,939. The entire disclosure is herein incorporated by reference into the present disclosure.

In some embodiments, the graft body comprises elongated demineralized bone fibers having an average length to average thickness ratio or aspect ratio of the fibers from about 50:1 to about 1000:1. In overall appearance the elongated demineralized bone fibers can be in the form of threads, narrow strips, or thin sheets. The elongated demineralized bone fibers can be substantially linear in appearance or they can be coiled to resemble springs. In some embodiments, the elongated demineralized bone fibers are of irregular shapes including, for example, linear, serpentine or curved shapes. The elongated bone fibers can be demineralized however some of the original mineral content may be retained when desirable for a particular embodiment.

In some embodiments, the graft body comprises elongated demineralized bone fibers and chips. In some embodiments, the ratio of fibers to chips or powders is from about 5, 10, 15, 20, 25, 30, 35, 40, or 45 fibers to about 30, 35, 40, 45, 50, 55, 60, 65, or 70 chips.

In some embodiments, the biocompatible material comprises demineralized bone matrix fibers and demineralized bone matrix chips in a 30:60 ratio. In some embodiments, the demineralized bone matrix material comprises demineralized bone matrix fibers and demineralized bone matrix chips in a ratio of 25:75 to about 75:25 fibers to chips.

In some embodiments, the demineralized bone material can be in the graft body and comprises from about 1 to about 70 micrometers particle size range or from about 125 to about 250 micrometer particle size range.

In some embodiments, the graft body may have a modulus of elasticity in the range of about $1 \times 10^2$ to about $6 \times 10^5$ dyn/cm$^2$, or $2 \times 10^4$ to about $5 \times 10^5$ dyn/cm$^2$, or $5 \times 10^4$ to about $5 \times 10^5$ dyn/cm$^2$. After the device is administered to the target site, the graft body may have a modulus of elasticity in the range of about $1 \times -10^2$ to about $6 \times 10^5$ dynes/cm$^2$, or $2 \times 10^4$ to about $5 \times 10^5$ dynes/cm$^2$, or $5 \times 10^4$ to about $5 \times 10^5$ dynes/cm$^2$.

In some embodiments, the substance may be designed to expand in vivo. Such an embodiment may be used to fill a space and create contact with congruent surfaces as it expands in vivo, for example for interbody fusion. Thus, in some embodiments, the bone graft delivery device may be used in the disc space, between implants, or inside a cage.

The graft body retains the substance in place by pressure against the graft body. The graft body thus may, in some embodiments, maintain particles of substance in close proximity (for example, where the graft body retains a substance comprising bone particles). Generally, the ratio of graft body material to substance for placement within the graft body may be low. For example, in some embodiments, the ratio of graft body material to substance, by weight, may be approximately 1:1,000, 1:100, 1:50, 1:25, 1:1, or any suitable ratio that may be higher or lower than these.

In some embodiments the substance delivered by the graft body may include or comprise an additive such as an angiogenesis promoting material or a bioactive agent. It will be appreciated that the amount of additive used may vary depending upon the type of additive, the specific activity of the particular additive preparation employed, and the intended use of the composition. The desired amount is readily determinable by one skilled in the art. Angiogenesis may be an important contributing factor for the replacement of new bone and cartilage tissues. In certain embodiments, angiogenesis is promoted so that blood vessels are formed at an implant site to allow efficient transport of oxygen and other nutrients and growth factors to the developing bone or cartilage tissue. Thus, angiogenesis promoting factors may be added to the substance to increase angiogenesis. For example, class 3 semaphorins, e.g., SEMA3, controls vascular morphogenesis by inhibiting integrin function in the vascular system, and may be included in the recovered hydroxyapatite.

In accordance with some embodiments, the substance may be supplemented, further treated, or chemically modified with one or more bioactive agents or bioactive compounds. Bioactive agent or bioactive compound, as used herein, refers to a compound or entity that alters, inhibits, activates, or otherwise affects biological or chemical events. For example, bioactive agents may include, but are not limited to, osteogenic or chondrogenic proteins or peptides; DBM powder; collagen, insoluble collagen derivatives, etc., and soluble solids and/or liquids dissolved therein; anti-AIDS substances; anti-cancer substances; antimicrobials and/or antibiotics such as erythromycin, bacitracin, neomycin, penicillin, polymycin B, tetracyclines, biomycin, chloromycetin, and streptomycins, cefazolin, ampicillin, azactam, tobramycin, clindamycin and gentamycin, etc.; immunosuppressants; antiviral substances such as substances effective against hepatitis; enzyme inhibitors; hormones; neurotoxins; opioids; hypnotics; anti-histamines; lubricants; tranquilizers; anti-convulsants; muscle relaxants and anti-Parkinson substances; anti-spasmodics and muscle contractants including channel blockers; miotics and anti-cholinergics; anti-glaucoma compounds; anti-parasite and/or anti-protozoal compounds; modulators of cell-extracellular matrix interactions including cell growth inhibitors and antiadhesion molecules; vasodilating agents; inhibitors of DNA, RNA, or protein synthesis; anti-hypertensives; analgesics; anti-pyretics; steroidal and non-steroidal anti-inflammatory agents; anti-angiogenic factors; angiogenic factors and polymeric carriers containing such factors; anti-secretory factors; anticoagulants and/or antithrombotic agents; local anesthetics; ophthalmics; prostaglandins; anti-depressants; anti-psychotic substances; anti-emetics; imaging agents; biocidal/biostatic sugars such as dextran, glucose, etc.; amino acids; peptides; vitamins; inorganic elements; co-factors for protein synthesis; endocrine tissue or tissue fragments; synthesizers; enzymes such as alkaline phosphatase, collagenase, peptidases, oxidases, etc.; polymer cell scaffolds with parenchymal cells; collagen lattices; antigenic agents; cytoskeletal agents; cartilage fragments; living cells such as chondrocytes, bone marrow cells, mesenchymal stem cells; natural extracts; genetically engineered living cells or otherwise modified living cells; expanded or cultured cells; DNA delivered by plasmid, viral vectors, or other member; tissue transplants; autogenous tissues such as blood, serum, soft tissue, bone marrow, etc.; bioadhesives; bone morphogenic proteins (BMPs); osteoinductive factor (IFO); fibronectin (FN); endothelial cell growth factor (ECGF); vascular endothelial growth factor (VEGF); cementum attachment extracts (CAE); ketanserin; human growth hormone (HGH); animal growth hormones; epidermal growth factor (EGF); interleukins, e.g., interleukin-1 (IL-1), interleukin-2 (IL-2); human alpha thrombin; transforming growth factor (TGF-beta); insulin-like growth factors (IGF-1, IGF-2); parathyroid hormone (PTH); platelet derived growth factors (PDGF); fibroblast growth factors (FGF, BFGF, etc.); periodontal ligament chemotactic factor (PDLGF); enamel matrix proteins; growth and differentiation factors (GDF); hedgehog family of proteins; protein receptor molecules; small peptides derived from growth factors above; bone promoters; cytokines; somatotropin; bone digesters; antitumor agents; cellular attractants and attachment agents; immuno-suppressants; permeation enhancers, e.g., fatty acid esters such as laureate, myristate and stearate monoesters of polyethylene glycol, enamine derivatives, alpha-keto aldehydes, etc.; and nucleic acids.

In certain embodiments, the bioactive agent may be a drug. In some embodiments, the bioactive agent may be a growth factor, cytokine, extracellular matrix molecule, or a fragment or derivative thereof, for example, a protein or peptide sequence such as RGD.

Sterilization

The bone graft delivery device may be sterilizable. In various embodiments, one or more components of the bone graft delivery device is sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

In various embodiments, gamma radiation is used in the terminal sterilization step, which involves utilizing ionizing energy from gamma rays that penetrates deeply in the device and/or graft body. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity. E-beam sterilization may be used, for example, when the device is included with a gel.

Other methods may also be used to sterilize the device and/or one or more components of the device, including, but not limited to, gas sterilization, such as, for example, with ethylene oxide or steam sterilization.

Methods of Use

In some embodiments, a method of making a bone graft delivery device is provided. The method comprises: adding DBM fibers to DBM powder to form a mixture; adding the mixture of DBM fibers and the DBM powder to a collagen slurry; drying the collagen slurry to form a sponge; and disposing the sponge within a biodegradable mesh bag. In some embodiments, the mineralized bone fibers are added to the collagen slurry. In some embodiments, the collagen slurry is poured into a mold before it is dried. In some embodiments, the drying comprises freeze drying the collagen slurry to form the sponge. In various embodiments, the polymer matrix is alternatively crosslinked. In some embodiments, the sponge is not disposed within the biodegradable mesh sealed bag.

In some embodiments, a method for treating a bone site is provided which includes providing a porous biodegradable bone graft body shaped to fit into a desired bone site, e.g., between two adjacent spinous processes. At least one bone delivery carrier is provided which may be attached to the porous biodegradable bone graft body. In some embodiments, two bone delivery carriers are provided, each being attached to either side of the porous biodegradable bone graft body. The porous biodegradable graft body retains the DBM material at, near, or in the bone site and facilitates transfer of cells into and out of the porous biodegradable graft body.

The porous biodegradable graft body delivers the substance or substances in vivo. Such delivery may be active, passive, by diffusion, or other. Active delivery may include the degradation or decomposition of the graft body with the interaction of body fluids, extracellular matrix molecules, enzymes or cells. It may also include the cleavage of physical and/or chemical interactions of substance from graft body with the presence of body fluids, extracellular matrix molecules, enzymes or cells. Further, it may comprise formation change of substances (growth factors, proteins, polypeptides) by body fluids, extracellular matrix molecules, enzymes or cells.

The porous biodegradable graft body is loaded with the substance for placement in vivo. The porous biodegradable graft body may be pre-loaded, thus loaded at manufacture, or may be loaded in the operating room or at the surgical site. Preloading may be done with any of the substances previously discussed including, for example, DBM, synthetic calcium phosphates, synthetic calcium sulfates, enhanced DBM, collagen, carrier for stem cells, and expanded cells (stem cells or transgenic cells). Loading in the operating room or at the surgical site may be done with any of these materials and further with autograft and/or bone marrow aspirate.

Any suitable method may be used for loading a substance in the porous biodegradable graft body in the operating room or at the surgical site. In some embodiments, the substance may be spooned into the porous biodegradable graft body, the substance may be placed in the porous biodegradable graft body using forceps, the substance may be loaded into the graft body using a syringe (with or without a needle), or the substance may be inserted into the graft body in any other suitable manner. Specific embodiments for loading at the surgical site include for vertebroplasty or for interbody space filler.

For placement, the substance or substances may be provided in the porous biodegradable graft body and the porous biodegradable graft body placed in vivo, for example at a bone defect. In one embodiment, the porous biodegradable graft body is placed in vivo by placing the porous biodegradable graft body in a catheter or tubular inserter and delivering the porous biodegradable graft body with the catheter or tubular inserter. The porous biodegradable graft body, with a substance provided therein, may be steerable such that it can be used with flexible introducer instruments for, for example, minimally invasive spinal procedures. For example, the osteoimplant may be introduced down a tubular retractor or scope, during XLIF, TLIF, or other procedures. In other embodiments, the porous biodegradable graft body (with or without substance loaded) may be placed in a cage, for example for interbody fusion.

In some embodiments, the porous biodegradable graft body may be prefilled with a substance for delivery and other compartments may be empty for filling by the surgeon.

In some embodiments, attachment mechanisms may be provided on the porous biodegradable graft body to couple the porous biodegradable graft body to a site in vivo.

The porous biodegradable graft body may be used in any suitable application. In some embodiments, the porous biodegradable graft body may be used in healing vertebral compression fractures, interbody fusion, minimally invasive procedures, posterolateral fusion, correction of adult or pediatric scoliosis, treating long bone defects, osteochondral defects, ridge augmentation (dental/craniomaxillofacial, e.g. edentulous patients), beneath trauma plates, tibial plateau defects, filling bone cysts, wound healing, around trauma, contouring (cosmetic/plastic/reconstructive surgery), and others. The device may be used in a minimally invasive procedure via placement through a small incision, via delivery through a tube, or other. The size and shape may be designed with restrictions on delivery conditions. In some embodiments, pieces of the graft body can be separated by pulling or tearing force applied along the separation assists and the pieces of the graft body can be used to surround the bone defect. For examples, 3 pieces of the torn porous biodegradable graft body can be placed around the bone defect to triangulate bone growth by the influx of cells, in, at or near the bone defect.

In some embodiments, the porous biodegradable graft body is flexible enough so that the graft body can be folded upon itself before it is implanted at, near or in the bone defect.

An exemplary application for using a bone graft delivery device as disclosed is fusion of the spine. In clinical use, the graft body and delivered substance may be used to bridge the gap between the transverse processes of adjacent or sequential vertebral bodies. The device may be used to bridge two or more spinal motion segments. The porous biodegradable graft body surrounds the substance to be implanted, and contains the substance to provide a focus for healing activity in the body.

In other applications, the device may be applied to transverse processes or spinous processes of vertebrae.

Generally, the device may be applied to a pre-existing defect, to a created channel, or to a modified defect. Thus, for example, a channel may be formed in a bone, or a pre-existing defect may be cut to form a channel, for receipt of the device. The graft body may be configured to match the channel or defect. In some embodiments, the configuration of the graft body may be chosen to match the channel. In other embodiments, the channel may be created, or the defect expanded or altered, to reflect a configuration of the graft body. The graft body may be placed in the defect or channel and, optionally, coupled using attachment mechanisms.

At the time just prior to when the device is to be placed in a defect site, optional materials, e.g., autograft bone marrow aspirate, autograft bone, preparations of selected autograft cells, autograft cells containing genes encoding bone promoting action, etc., can be combined with the graft body and/or with a substance provided within the graft body. The device can be implanted at the bone repair site, if desired, using any suitable affixation member, e.g., sutures, staples, bioadhesives, screws, pins, rivets, other fasteners and the like or it may be retained in place by the closing of the soft tissues around it.

In some embodiments, the porous biodegradable graft body may be a single or multi-compartment structure capable of at least partially retaining a substance provided therein until the porous biodegradable graft body is placed at a surgical site. The porous biodegradable graft body may include separation-assist lines such as perforations. Upon placement, the substance may be released (actively or passively) to the surgical site. The porous biodegradable graft body may participate in, control, or otherwise adjust, the release of the substance. The device may be used to control availability of a substances provided within the device to cells and tissues of a surgical site over time.

Although the invention has been described with reference to preferred embodiments, persons skilled in the art will recognize that changes may be made in form and detail without departing from the spirit and scope of the invention.

What is claimed is:

1. A bone graft delivery device comprising: a porous biodegradable graft body for inducing bone growth at a surgical site, the porous biodegradable graft body having demineralized bone matrix (DBM) fibers disposed within the porous biodegradable body, and DBM powder disposed on and adhering to the DBM fibers, the DBM powder having a particle size of about 25 to about 95 microns, wherein the porous biodegradable graft body facilitates transfer of cells into and out of the porous biodegradable graft body to induce bone growth at the surgical site, and an adhesive to cause the DBM powder to adhere to the DBM fibers, wherein the adhesive does not contain collagen.

2. A bone graft delivery device of claim 1, wherein (i) the device further comprises mineralized bone fibers; or (ii) the DBM fiber and DBM powder are disposed in a collagen matrix that is disposed in the porous biodegradable graft body.

3. A bone graft delivery device of claim 2, wherein (i) the DBM powder adheres to the DBM fibers and the mineralized bone fibers via a surface located on the fibers; or (ii) the collagen matrix is slidably disposed within the porous biodegradable graft body.

4. A bone graft delivery device of claim 2, wherein the average length of the DBM fibers and the mineralized bone fibers are from about 0.25 cm to about 10 cm and the average length of the DBM fibers and the mineralized bone fibers are from about 0.50 cm to about 3 cm.

5. A bone graft delivery device of claim 2, wherein the ratio of mineralized bone fibers to DBM powder is about 25:75 to about 75:25 W/W, W/V or V/V.

6. A bone graft delivery device of claim 2, wherein the device comprises DBM fibers and mineralized fibers in a ratio of 40:60 to about 90:10 W/W, W/V or V/V.

7. A bone graft delivery device of claim 1, wherein the ratio of DBM fibers to DBM powder is about 40:60 to about 90:10 W/W, W/V or V/V.

8. A bone graft delivery device of claim 1, wherein the porous biodegradable graft body comprises a mesh sealed bag comprising pores at about 100 to about 200 microns.

9. A bone graft delivery device of claim 8, wherein the mesh sealed bag is sealed via heat sealing, stitching, adhesion, tying, fold lock and cinching.

10. A bone graft delivery device of claim 1, wherein the porous biodegradable graft body comprises a mesh sealed bag comprising natural materials, synthetic polymeric resorbable materials, synthetic polymeric non-resorbable materials or a combination thereof.

11. A bone graft delivery device of claim 1, wherein the porous biodegradable graft body comprises a mesh sealed bag comprising human skin, collagen, human hair, polyethylene glycol, chitosan, alginate, cellulose, hyaluronic acid, keratin, a biodegradable polymer, poly(lactide-co-glycolide), fat, bone, or a combination thereof.

12. A bone graft delivery device of claim 1, wherein the ratio of DBM fibers to DBM powder is about 40:60.

13. A bone graft delivery device of claim 1, wherein the DBM fibers are fully demineralized.

14. A bone graft delivery device of claim 1, wherein the adhesive comprises cement, cyanoacrylate, silicones, and/or cellulosic binders.

15. A bone graft delivery device comprising: a porous biodegradable graft body for inducing bone growth at a surgical site, the porous biodegradable graft body having demineralized bone matrix (DBM) fibers and DBM powder disposed on and adhering to the DBM fibers, and the DBM fibers are suspended in a polymer matrix that is disposed within the porous biodegradable body, the DBM powder having a particle size of about 25 to about 95 microns, wherein the porous biodegradable graft body facilitates transfer of cells into and out of the porous biodegradable graft body to induce bone growth at the surgical site, and an adhesive to cause the DBM powder to adhere to the DBM fibers, wherein the adhesive does not contain collagen.

16. A bone graft delivery device of claim 15, wherein the graft further comprises mineralized bone fibers also suspended in the polymer matrix.

17. A bone graft delivery device of claim 15, wherein the polymer matrix is a porous sponge and comprises collagen, chitosan, alginate or hyaluronic acid.

18. A bone graft delivery device of claim 15, wherein the device further comprises bone morphogenic proteins (BMPs), growth factors, antibiotics, angiogenesis promoting materials, and/or bioactive agents.

19. A method of making a bone graft delivery device, the method comprising: adding DBM fibers to DBM powder and adding an adhesive to form a mixture; adding the mixture of DBM fibers and the DBM powder to a collagen slurry, the DBM powder having a particle size of about 25 to about 95 microns; drying the collagen slurry to form a sponge; and disposing the sponge within a biodegradable mesh bag, wherein the adhesive does not contain collagen.

20. A method of making a bone graft delivery device of claim 19, wherein (i) mineralized bone fibers are added to the collagen slurry; (ii) the collagen slurry is poured into a mold before it is dried; or (iii) the drying comprises freeze drying the collagen slurry to form the sponge.

* * * * *